United States Patent

Slamin et al.

Patent Number: 5,766,255
Date of Patent: Jun. 16, 1998

[54] MODULAR JOINT PROSTHESIS STABILIZATION AND AUGMENTATION SYSTEM

[75] Inventors: John E. Slamin, Wrentham; Michael J. O'Neil, West Barnstable, both of Mass.; Jason T. Gulbinas, Broad Brook, Conn.

[73] Assignee: Johnson & Johnson Professional, Inc., Raynham, Mass.

[21] Appl. No.: 772,966

[22] Filed: Dec. 23, 1996

[51] Int. Cl.⁶ .................................................. A61F 2/38
[52] U.S. Cl. ............................................................. 623/20
[58] Field of Search .................................. 623/16, 18, 20

[56] References Cited

U.S. PATENT DOCUMENTS

| | | |
|---|---|---|
| 1,664,566 | 4/1928 | Marshall . |
| 1,816,970 | 8/1931 | Hess . |
| 2,490,364 | 12/1949 | Livingston . |
| 2,616,328 | 11/1952 | Kingsmore . |
| 3,076,453 | 2/1963 | Tronzo ................................. 128/92 |
| 4,081,866 | 4/1978 | Upshaw et al. ..................... 3/1.911 |
| 4,209,861 | 7/1980 | Walker et al. ...................... 3/1.911 |
| 4,312,614 | 1/1982 | Palmer et al. ......................... 411/44 |
| 4,353,135 | 10/1982 | Forte et al. ......................... 3/1.911 |
| 4,711,232 | 12/1987 | Fischer et al. ....................... 128/92 |
| 4,731,086 | 3/1988 | Whiteside et al. ................... 623/20 |
| 4,769,039 | 9/1988 | Horber .................................. 623/20 |
| 4,822,366 | 4/1989 | Bolesky ............................... 623/20 |
| 4,878,791 | 11/1989 | Kurihara et al. ..................... 411/55 |
| 4,892,547 | 1/1990 | Brown ................................. 623/20 |
| 4,936,847 | 6/1990 | Manginelli ........................... 623/23 |
| 4,950,298 | 8/1990 | Gustilo et al. ....................... 623/20 |
| 4,971,500 | 11/1990 | Benoit et al. ....................... 411/182 |
| 5,108,446 | 4/1992 | Wagner et al. ...................... 623/22 |
| 5,152,796 | 10/1992 | Slamin ................................. 623/20 |
| 5,176,684 | 1/1993 | Ferrante et al. ..................... 606/86 |
| 5,201,768 | 4/1993 | Caspari et al. ...................... 623/20 |
| 5,207,711 | 5/1993 | Caspari et al. ...................... 623/20 |
| 5,222,984 | 6/1993 | Forte ................................... 623/22 |
| 5,268,001 | 12/1993 | Nicholson et al. .................. 606/72 |
| 5,326,359 | 7/1994 | Oudard ................................ 623/20 |
| 5,370,693 | 12/1994 | Kelman et al. ...................... 623/16 |
| 5,387,240 | 2/1995 | Pottenger et al. ................... 623/20 |
| 5,405,395 | 4/1995 | Coates ................................. 623/20 |
| 5,549,685 | 8/1996 | Hayes .................................. 623/20 |
| 5,549,687 | 8/1996 | Coates et al. ....................... 623/20 |
| 5,556,433 | 9/1996 | Gabriel et al. ...................... 623/20 |
| 5,609,645 | 3/1997 | Vinciguerra ......................... 623/20 |

FOREIGN PATENT DOCUMENTS

| | | | |
|---|---|---|---|
| 0536457 | 4/1993 | European Pat. Off. ............. 623/20 |
| 2223174 | 4/1990 | United Kingdom . | |

*Primary Examiner*—Michael J. Milano
*Assistant Examiner*—Tram Anh T. Nguyen
*Attorney, Agent, or Firm*—Nutter, McClennen & Fish, LLP

[57] ABSTRACT

A modular joint prosthesis system includes an articulation component having a bone engaging surface and an opposed articulation surface. Fixation peg members and/or augmentation components are selectively attachable to the bone engaging surface of the articulation component. The articulation component may be a cruciate sacrificing femoral component of a knee prosthesis.

32 Claims, 10 Drawing Sheets

MODULAR JOINT PROSTHESIS STABILIZATION AND AUGMENTATION SYSTEM

BACKGROUND OF THE INVENTION

The invention relates to joint prostheses having enhanced stability and modularity.

Joint arthroplasty is a well known surgical procedure by which a diseased and/or damaged natural joint is replaced by a prosthetic joint. Joint arthroplasty is commonly performed for knees, hips, elbows, and other joints. The health and condition of the joint to be replaced dictate the type of prosthesis that can suitably be used to replace the natural joint. For example, knee prostheses, and particularly femoral components of knee prostheses, are available in different designs to meet the needs of varying patient conditions.

Some femoral components for knee joint prostheses are known as cruciate retaining femoral components since they are useful as a prosthesis component where a patient's cruciate ligaments are not sacrificed during a knee arthroplasty procedure. This type of femoral component typically has fixation pegs integrally mated upon the medial and lateral distal flats of the superior surface of the prosthesis to stabilize the prosthesis upon mounting to the femur. The cruciate ligaments also contribute to the stability of the artificial knee joint.

Another type of femoral component for a knee joint prosthesis is known as a cruciating sacrificing femoral component. This type of prosthesis component is useful where the patient's cruciate ligaments are non-functional or must be removed in the course of a knee arthroplasty procedure. Cruciate sacrificing femoral components typically have an intercondylar notch formed on a superior, bone engaging surface of the femoral component. This structure is in the form of a box, having substantially vertical medial, lateral, anterior and posterior walls, and a substantially horizontal superior wall. The intercondylar notch is mounted within the patient's femur to stabilize the prosthesis. Typically, an aperture is formed in the superior wall of the intercondylar notch and it is useful to mate a femoral stem to the femoral component. The femoral stem helps to anchor the femoral component to a patient's femur, and to contribute stability to the artificial joint.

Femoral component fixation in cruciate substituting total knee replacement surgery is sometimes achieved through cement attachment of the femoral component to the prepared femur while stability is imparted to the femoral component by the intercondylar notch, femoral chamfer cuts, and the optional attachment of femoral stems or rods. It is sometimes possible for cruciate substituting femoral components to loosen and thus contribute to the need for total knee replacement surgery and enhanced stabilization of the prosthesis.

In some instances, due to disease or trauma, insufficient healthy bony mass exists at the distal end of a bone (e.g., the femur) to which a joint prosthesis is to be secured. In arthroplasty procedures, it is often necessary to remove additional portions of bone (e.g., the femur) in an asymmetrical manner, to ensure sufficient anchoring and proper fit for a prosthesis. In the example of knee joint arthroplasty, it is sometimes necessary to augment the superior portion of the femoral component prosthesis to add additional thickness to the prosthesis to compensate for any removed bony tissue. The femoral component can be augmented by adding augmenting blocks of appropriate shapes and sizes to the superior surface thereof. Various types of augmentation blocks are known to those having ordinary skill in the art. An exemplary augmentation system is disclosed in U.S. Pat. No. 4,936,847 (Manginelli).

The stability of cruciate substituting femoral components can be reduced with the installation of augmentation components, some of which can approach the height of the intercondylar notch. Since these prostheses rely largely on the intercondylar notch for secure engagement within the femur, any relative decrease in the height of the intercondylar notch above the medial and lateral distal flats can decrease the stability of the femoral component.

Many existing knee prosthesis designs do not offer the ability to selectively enhance prosthesis stability of the femoral component. Prosthesis stability can be a problem of particular concern in revision cruciate substituting femoral components that require augmentation systems. It would thus be desirable to offer improved joint prostheses components which offer surgeons increased versatility to achieve prosthesis stability.

SUMMARY OF THE INVENTION

The present invention relates to modular joint prostheses that offer surgeons enhanced versatility to achieve prosthesis component stability. In particular, the prosthesis system of the invention enables surgeons to selectively add fixation stabilizing members and/or augmentation components. While the invention is applicable to a variety of joint prosthesis components in which stabilization is important and augmentation is sometimes necessary, the invention is described herein with respect to femoral components of knee prostheses.

The invention comprises a modular joint prosthesis that includes an articulation component, such as a femoral component of a knee prosthesis, having a first, bone-engaging surface and a second, articulation surface. At least one securement cavity is formed in the first surface, and most preferably a securement cavity is formed on each of the medial and lateral distal flats of the femoral component. The system also includes at least one elongate fixation peg member, each of which is selectively mateable to the securement cavity in the first surface to provide enhanced prothesis stability. The fixation pegs each have distal and proximal ends and include an axial bore which may include internal fixation structures such as internal threads. The system also includes a collet member for each fixation peg, and each collet member has two or more expandable elements that are able to selectively engage the sidewalls of one of the securement cavities. A bore preferably extends through the collet, and at least a proximal portion of the bore may include fixation structures such as internal threads. One or more expansion pins are also provided and each has a distal end that is able to expand the collet and a proximal end which may include a structure, such as external threads, which facilitates mating within the bores of the fixation peg member and the collet member.

In use, the fixation peg is positioned over a securement cavity and the expansion element of the collet is disposed within the cavity. The expansion pin is then inserted within the collet and the fixation peg to positively engage the peg and to expand the expandable elements of the collet such that they engage the walls of the cavity to secure the peg to the prosthesis.

One or more augmentation blocks, of desired shapes and sizes, may be provided to fit between the first surface of the femoral component and the fixation pegs such that the augmentation block and the fixation pegs are together selectively affixed to the articulation component. This system is particularly useful with cruciate substituting femoral components of knee joint prosthesis to provide added prosthesis stability.

In one embodiment the collet members are separate from the fixation pegs and the expansion pins engage both the collet and the fixation peg. In another embodiment the collet members are integral with and are formed on a distal end of the fixation pegs.

DETAILED DESCRIPTION OF THE INVENTION

The invention provides a joint prosthesis system 10 that offers enhanced intraoperative versatility and modularity to improve femoral component fixation and stability. The invention is particularly applicable to cruciate substituting femoral components. For illustrative purposes, the present invention is described with reference to an anticipated use with a femoral component of a knee joint prosthesis. It is understood, however, that the invention can be adapted for use with a variety of joint prostheses. A particular advantage of the present invention, which lends itself to use with various types of joint prostheses, is the ease with which fixation elements and augmentation pieces can be secured to a prosthesis.

Figure 1:
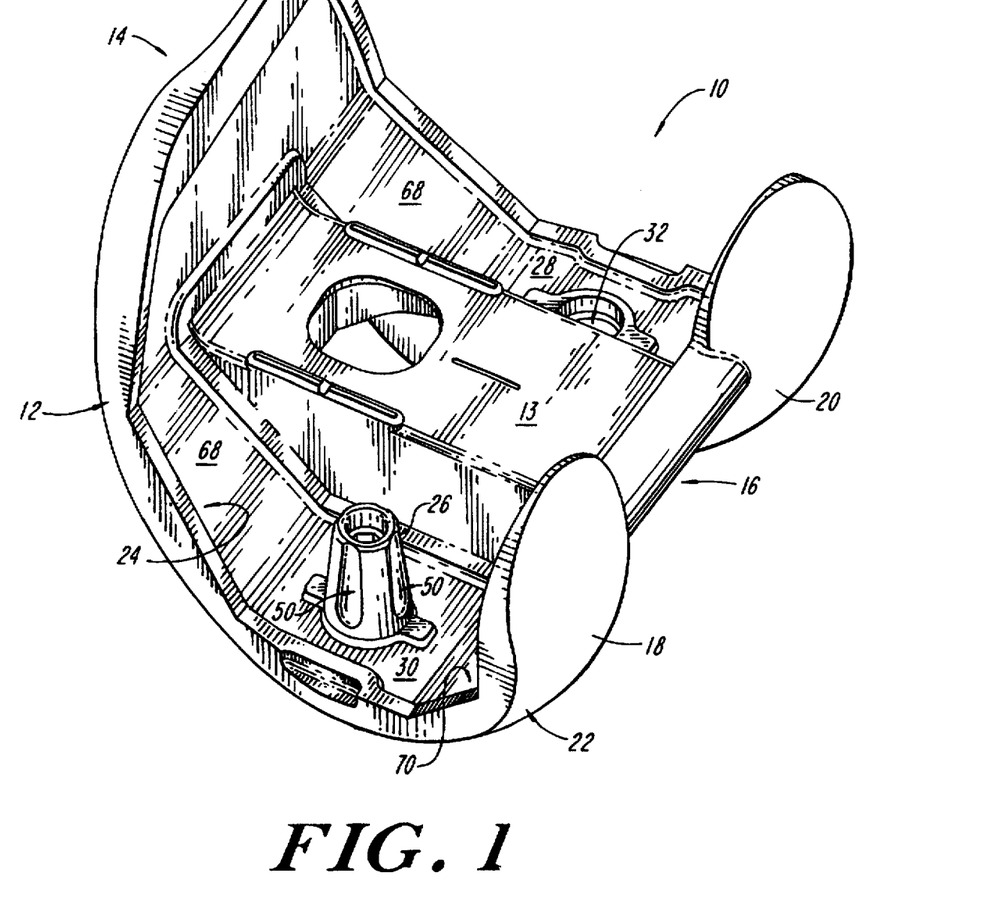
FIG. 1 is an isometric view of a knee joint prosthesis femoral component having a modular stabilizing peg according to the present invention.
Figure 2A:
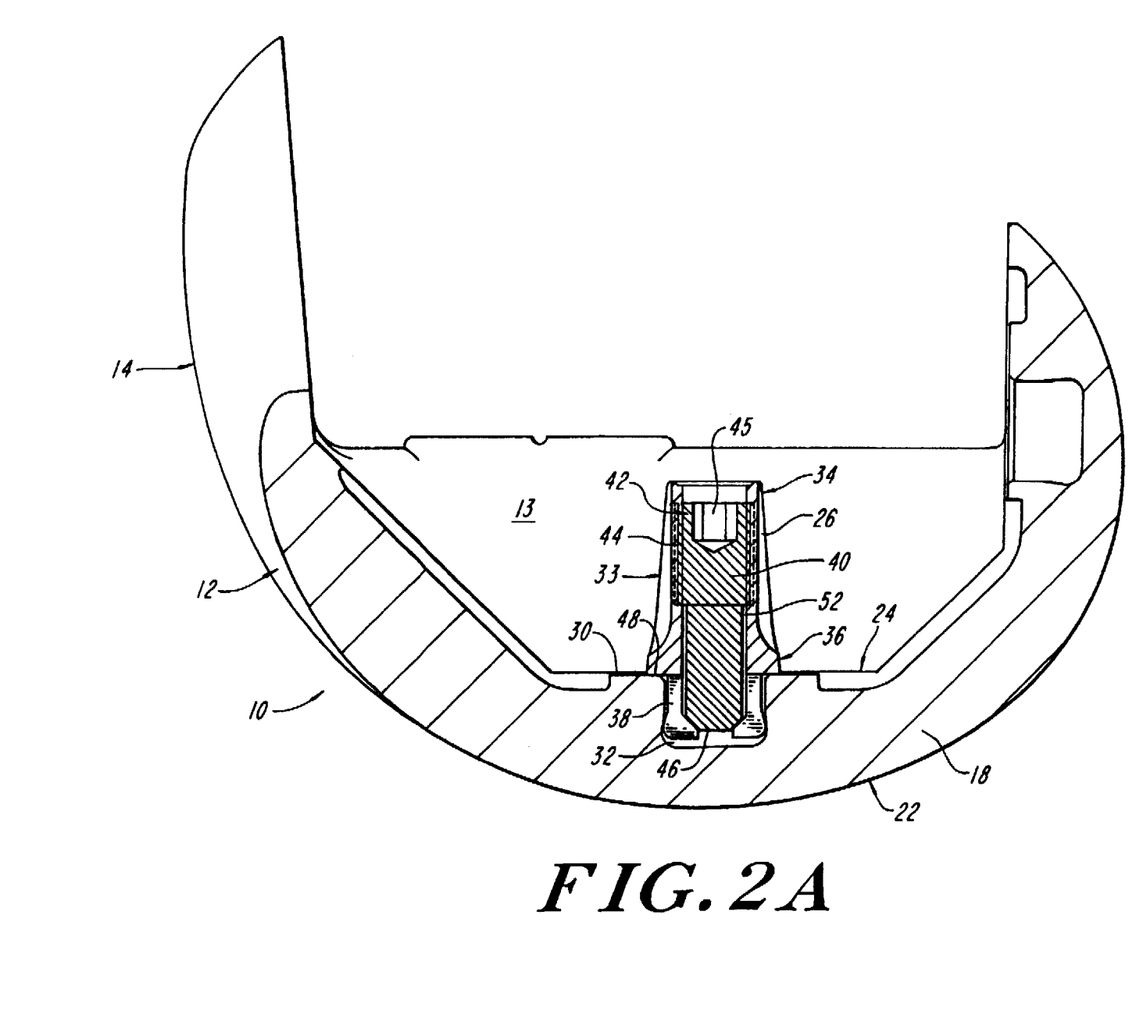
FIG. 2A is a sectional view of the prosthesis shown in FIG. 1.
Figure 2B:
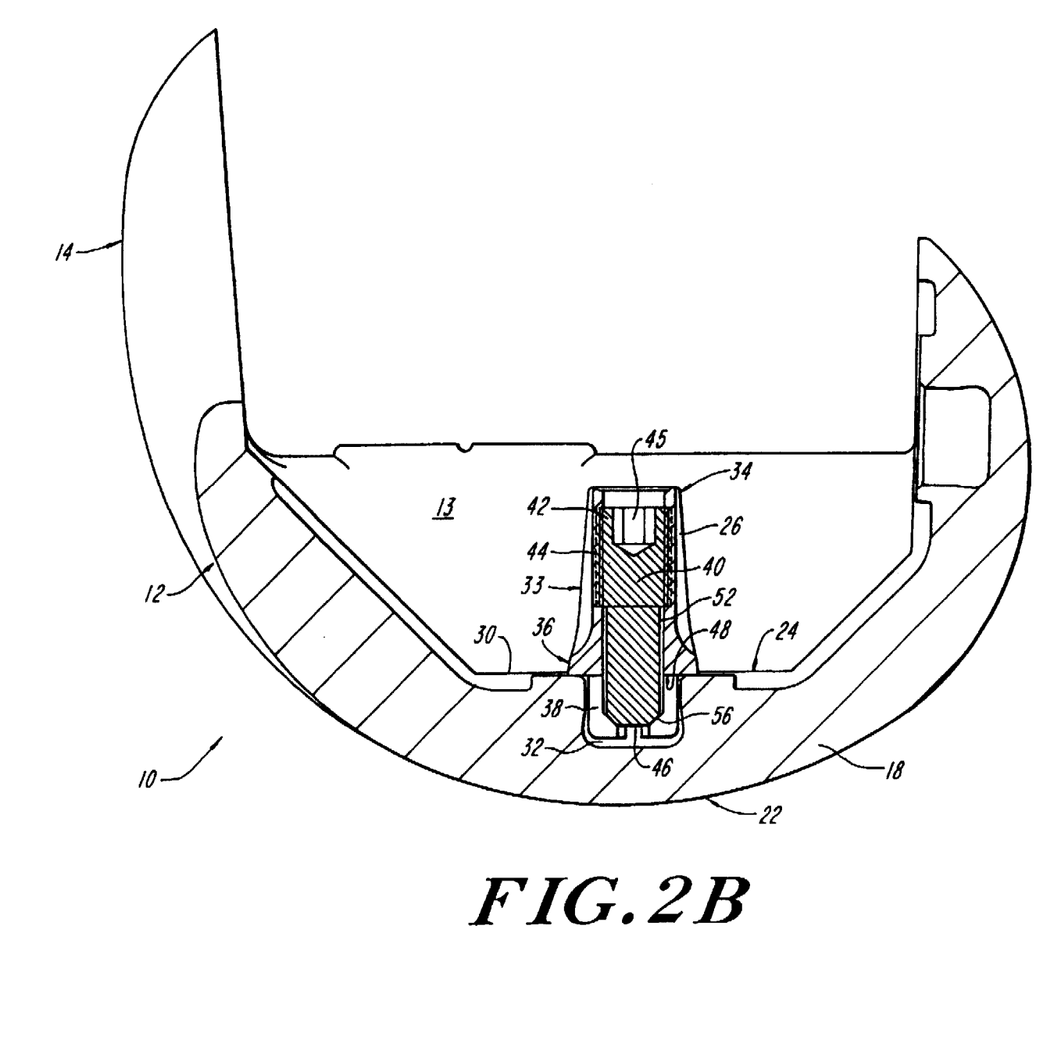
FIG. 2B is a sectional view of the prosthesis shown in FIG. 1, illustrating the collet in a non-expanded condition.

As noted above, and as illustrated in FIGS. 1 through 6, the invention is particularly applicable to use with cruciate substituting femoral components. FIG. 1 illustrates the prosthesis system 10 of the invention in which a cruciate substituting femoral component 12 has an intercondylar notch 13, anterior and posterior portions 14, 16 and condyles 18, 20. Each condyle includes an inferior articulation surface 22 and an opposed superior bone engaging surface 24. FIGS. 2A and 2B illustrate that the lateral distal flat 30 includes a securement cavity 32, and a similar cavity (not shown) is formed in the medial distal flat 28. Fixation pegs 26 are selectively mounted within securement cavities 32 upon the medial and lateral distal flats 28, 30 of superior surface 24, on opposite sides of intercondylar notch 13.

As illustrated in FIGS. 2A through 4, the system includes modular, selectively mountable fixation pegs 26. The fixation pegs 26 are substantially elongate members having a peg body 33 with proximal and distal ends 34, 36. Preferably, a bore 52 extends between the proximal and distal ends of the fixation peg. Further, an expansion collet 38 is integral with and is disposed distally of the distal end 36 of peg body 33. The system also includes a supply of expansion pins 40 having a proximal end 42, including external threads 44, and a distal, collet expanding end 46. Although the illustrated expansion pins include external threads, it is understood that alternative surface features may exist on the expansion pins, instead of threads, to permit positive engagement with the bore 52 of the fixation peg 26.

As noted above, the modularity of the fixation pegs is an important feature of the invention. Since fixation pegs need not be installed on all cruciate sacrificing femoral components, the modularity offered by this invention gives the surgeon the option to attach fixation pegs to a prosthesis to be implanted.

Fixation pegs can be selectively mounted upon a prosthesis by simply placing the expansion collet end 38 of peg 26 within one of the securement cavities. Thereafter, set screw 40 is inserted within the proximal end 34 of the fixation peg and into bore 52. In an embodiment in which a threaded expansion pin is utilized, the expansion pin is advanced within the bore and external threads on the screw mate with complementary threads in the bore. Further advancement of the expansion pin causes the distal end of the expansion pin to expand collet 38 so that the collet interferingly engages the walls of cavity 32 to secure the fixation peg to the prosthesis.

The overall length of the fixation pegs can vary depending upon the anatomical requirements of a patient, the dimensions of prostheses components, and whether the peg is to be used with or without any augmentation block. Generally, the overall length of the peg can be from 2 to 60 millimeters, and more preferably from about 10 to 50 millimeters. The length of the collet end 38 of peg 26 should be such that it is slightly less than the depth of cavity 32, allowing distal base 48 of peg 26 to rest on superior surface 24 of the femoral component. The length of the collet is generally about 2 mm to 20 mm. Further, the fixation peg preferably decreases in diameter from distal end 36 to proximal end 34. The diameter at base 48 is about 4 mm to 10 mm, while the diameter at proximal end 34 is about 2 mm to 8 mm. External surface features 50, such as axial grooves, axial ribs, annular grooves or annular ribs, can be formed in the external surface of the peg to enhance fixation of the prosthesis within bone.

Figure 5A:
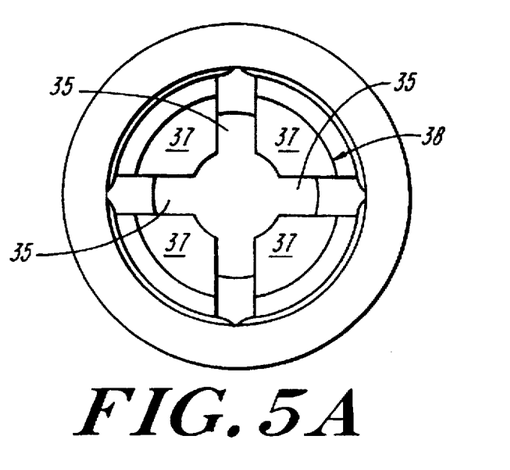
FIG. 5A is a bottom view of a fixation peg useful with the prosthesis shown in FIG. 1.

FIG. 5A is a bottom view of fixation pin 26, illustrating the expansion collet 38. The collet 38 is preferably slotted, with two perpendicular slots 35 formed therein that separate the collet into four substantially triangular shaped wedges 37. Although not illustrated, an interior portion of collet 38 is angled inwardly to enable the internal geometry of the collet to cooperate with the distal end 46 of expansion pin 40 to cause wedges 37 to expand and to separate from one another when the distal end of the expansion pin is forced into engagement with the corresponding internal surfaces of the wedges.

It is understood that it is not necessary that the collet have two slots disposed therein to form four substantially triangular wedges 37. It will be readily apparent to one having ordinary skill in the art that the collet may have one or more slots disposed therein.

Figure 5B:
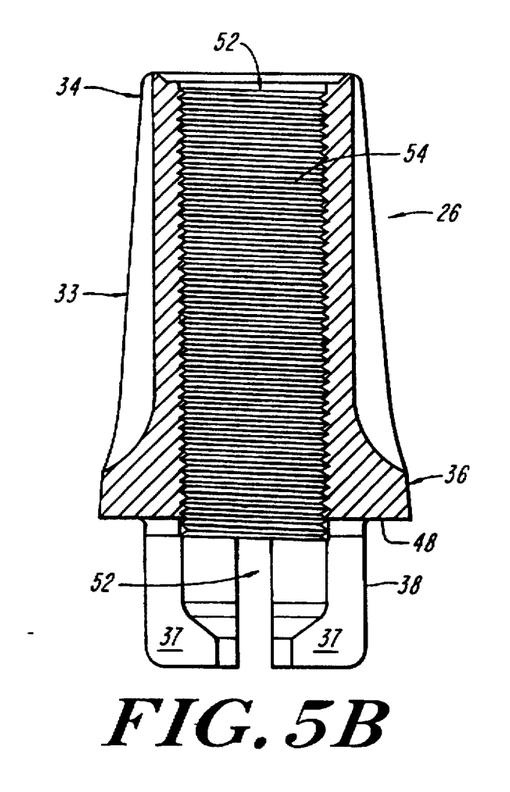
FIG. 5B is a sectional view of the collet shown in FIG. 5A.

FIG. 5B is a sectional view of peg 26, showing a bore 52 that extends the length of the body 33 of peg 26. Bore 52 preferably includes internal threads 54 that are able to mate with complementary external threads 44 of expansion pin 40. Although bore 52 includes threads 54 in an illustrated embodiment, it is understood that other structures may be formed within bore 52 to facilitate engagement with complementary external structures on expansion pin 40.

Expansion pins 40 are of a length sufficient to enable them to fit within peg 26 to the extent necessary to expand collet 38. The expansion pin includes a proximal end 42, having external threads 44 that are mateable with internal threads 54 of bore 52, and a distal end 46. The proximal end of the expansion pin may include a structure or mechanism, such as a hex head 45, that cooperates with an installation tool to enable it to be advanced into bore 52. Distal end 46 preferably has a geometry that will cause expansion of the distal stem of the collet. The distal end 46 of pin 40 can include a radius tip 56, a dogged end (not shown) or similar geometries.

Although the expansion pins 40 are described as being threaded members that threadingly engages internal threads 54 within bore 52, it is understood that other fixation structures and techniques may be utilized to maintain the expansion pins within the bore 52 and to expand collet 38. As noted above, internal structures may be formed within bore 52 that accommodate complementary surface features on expansion pin 40 to enable mechanical engagement of the components.

Figure 3:
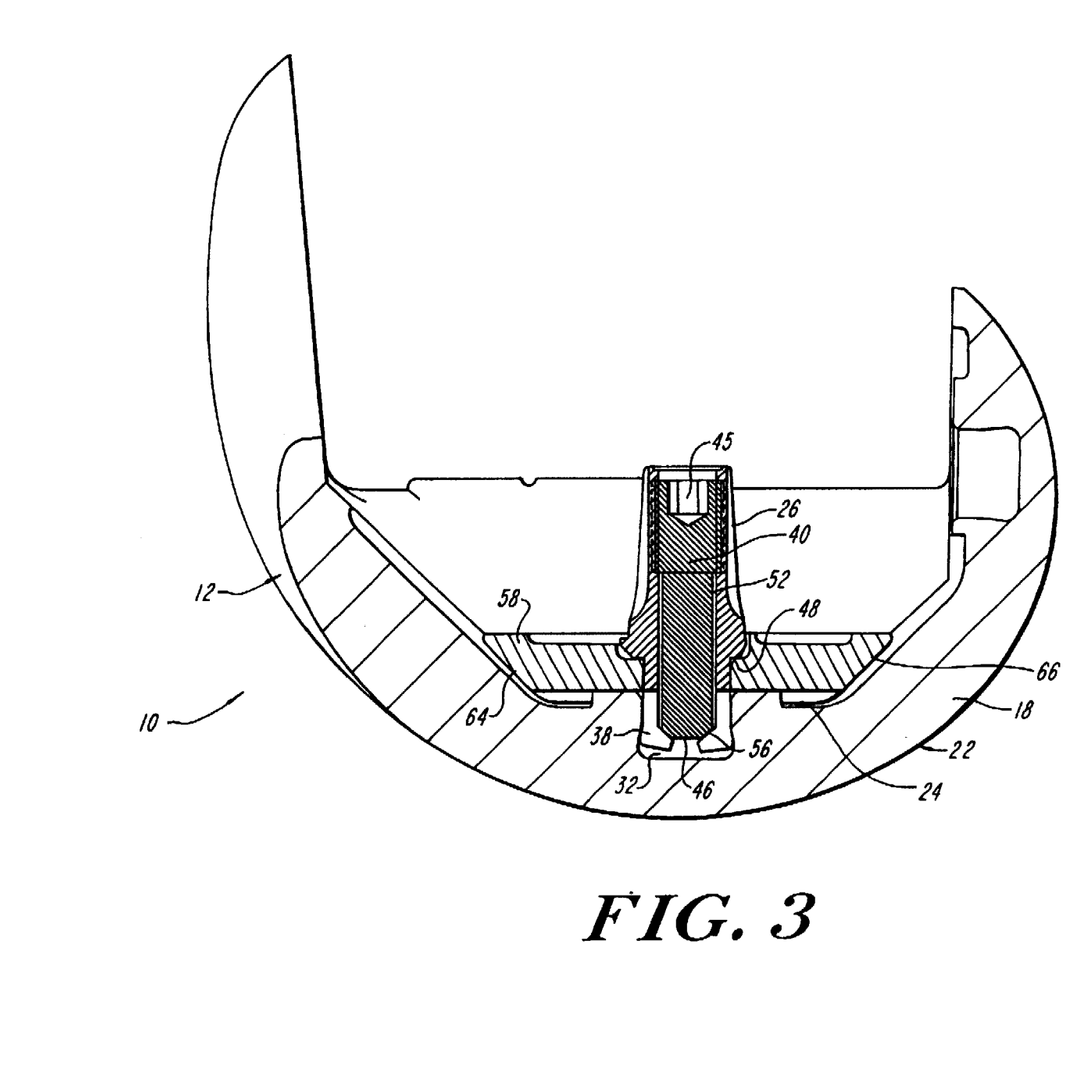
FIG. 3 is a sectional view of an alternative prosthesis system, similar to that shown in FIG. 2A, but also including an augmentation block.
Figure 4:
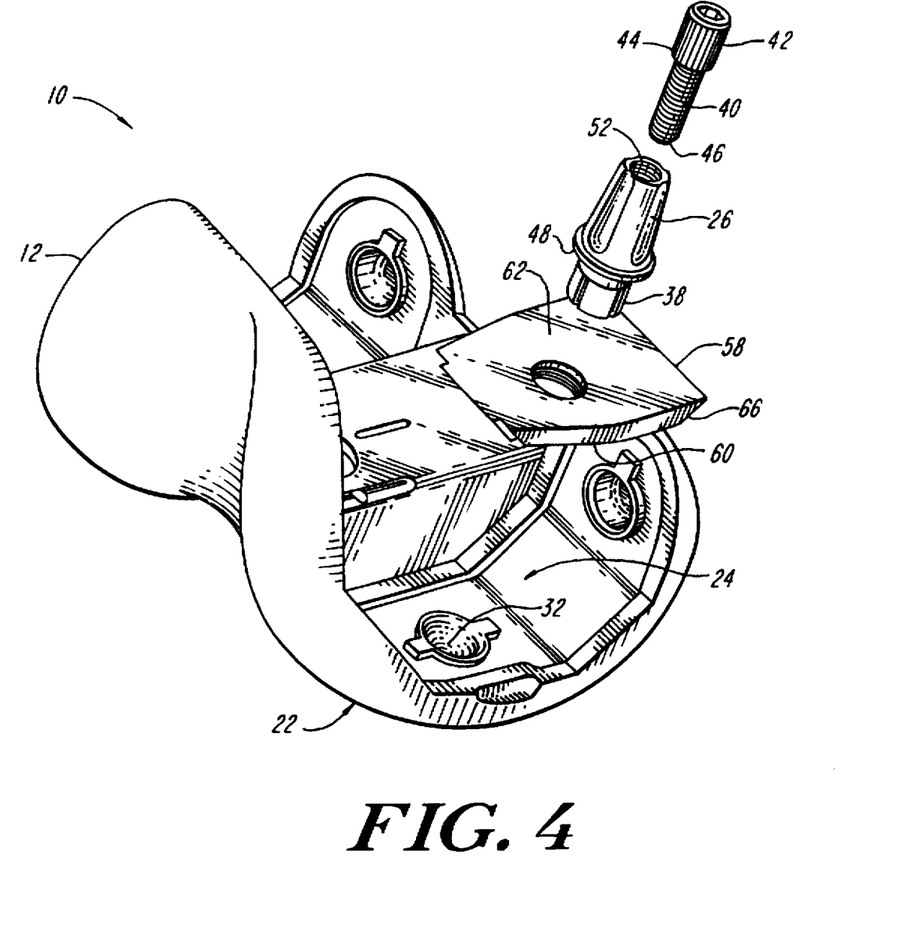
FIG. 4 is an exploded view of the prosthesis shown in FIG. 3.

In another embodiment, illustrated in FIGS. 3 and 4, the modular system 10 of the invention may also include an augmentation block 58 that is secured on superior surface 24 of femoral component 12, between the femoral component 12 and the fixation peg 26. Augmentation blocks of various designs are well known in the art and are commonly used to facilitate proper seating of prosthesis components within a patient when insufficient bony mass exists in certain areas of the patient's bone upon which the prosthesis is to be mounted.

Figure 6:
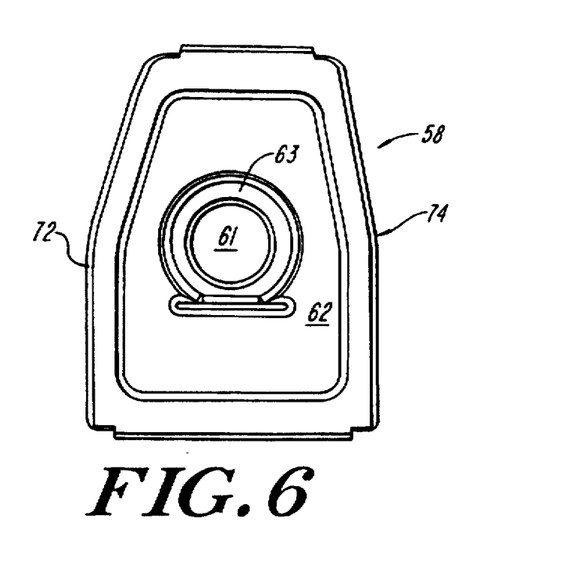
FIG. 6 is a top view of an augmentation block of the type shown in FIG. 4.

The augmentation block 58 illustrated in FIGS. 3, 4 and 6 is adapted to mount on the superior surface 24, on either the medial or lateral distal flats 28, 30 of a femoral component 12 of an artificial knee joint. Block 58 may be adapted for use in either left or right side knee prostheses. An augmenting block suitable for a left side prosthesis can mount upon either the medial or lateral inferior condylar surfaces, and an augmenting block suitable for a right side prosthesis can mount upon either the medial or lateral inferior condylar surfaces of the prosthesis. As illustrated, block 58 has a first (distal) surface 60 and a second (proximal) surface 62 and an aperture 61 extending between these surfaces. A recessed area 63 may surround the aperture 61. The area of the proximal surface 62 preferable is greater than the area of the distal surface 60 in order for the block to conform to the geometry of the inner condylar surface of a knee joint femoral component.

Augmenting block 58 has two opposed, canted surfaces 64, 66 that can be either posterior or anterior surfaces, depending upon whether the augmentation block is mounted on the medial or lateral side, or on a left or right side prosthesis. Preferably, surfaces 64, 66 are canted as such that each surface slopes inwardly from the proximal surface 62 to the distal surface 60 as shown in FIGS. 4 and 6. The angle of the canted surfaces 64, 66 can vary as will be appreciated by those having ordinary skill in the art. Preferably, the angle of surfaces 64, 66 corresponds to the angle of the anterior and posterior chamfers 68, 70 of the femoral component to enable proper seating of the augmenting block 58 within a femoral component.

Augmenting block 58 further includes surfaces 72, 74 which correspond to either medial or lateral facing surfaces, depending upon whether the augmentation block 58 is used on the lateral or medial side of a prosthesis, or in a left or right side prosthesis. Side surfaces 72, 74 preferably are substantially vertical and extend at a right angle to the plane of the proximal or distal surfaces 62, 60.

As illustrated in FIG. 3 augmentation block 58 is adapted to mount on a prosthesis component, such as the medial or lateral distal flats 28, 30, such that the distal surface 60 of block 58 contacts the superior surface 24 of femoral component 12. The distal end of expansion collet 38 of fixation peg 26 preferably extends through aperture 61 and beyond the distal surface 60 of block 58 by a distance sufficient to enable collet 38 to fit within a securement cavity 32 disposed in a surface of the femoral component to be augmented. The frictional and/or mechanical engagement of the collet with cavity 32 enables the augmentation system to be secured to an appropriate surface of the femoral component. The distance by which distal stem extends beyond the distal surface of the block can vary depending upon the requirements of a given application. Typically, this distance is about 0.155 to 0.175 inch and most preferably about 0.165 inch. One of ordinary skill in the art will appreciate that the length of the distal stem should not be so great that its distal end contacts the bottom of cavity 32.

As noted above, an expansion pin 40 controls the expansion (and, optionally, the contraction) of the distal stem of collet 58. In one embodiment, where the expansion pin is a threaded screw, tightening of the screw expands the distal stem of the collet, while loosening screw enables a once expanded collet to contract. When collet 38 is in a non-expanded condition there is little or no frictional and/or mechanical engagement between collet 38 and securement cavity 32; the augmentation block can be freely removed and inserted into securement cavity 32 in this condition. Conversely, when the collet 38 is in the expanded condition, as shown in FIG. 3, sufficient frictional and/or mechanical engagement exists between the collet 38 and the walls of the securement cavity 32 to enable the augmentation block and the fixation peg to be held firmly on the prosthesis component.

As noted above, the invention described above can be used with or without augmentation blocks. Further, because the fixation pegs are not permanently installed upon the prosthesis, they can be selectively affixed to the prosthesis at the option of the surgeon.

The dimensions of the various components of system 10 can vary. It is important, however, that the relative dimensions of the components be such that collet 38, in the non-expanded condition shown in FIG. 2B, be able to fit within the securement cavity (and, where applicable through augmentation block aperture 61) without excess friction or interference. Upon expansion of the collet, as shown in FIG. 2A, the outer walls of wedges 37 should firmly engage the inner walls of securement cavity 32 to prevent dislodgement or movement of the fixation peg. The preferred tensile attachment force of the collet to the prosthesis should be in the range of about 50 to 500 kg. The dimensions of these components will vary depending upon the requirements of a given application, and one of ordinary skill in the art can readily determine the appropriate relative dimensions. Generally, the diameter of the collet in the non-expanded condition is approximately 0.240 to 0.260 inch, and preferably it is about 0.250 inch. The diameter of the collet in the expanded condition preferably is about 0.010 to 0.020 inch greater than the diameter in the non-expanded condition. The diameter of the securement cavity 32 is sufficient to yield a secure interference fit between the collet and the cavity when the collet is expanded. Preferably, the cavity has a diameter of about 0.26 inch ± 0.10 inch. The depth of the mounting cavity can vary, as will be understood by those of ordinary skill in the art, but preferably the depth is about 0.18 to 0.26 inch. As noted above, the collet 38 should not engage the bottom wall of cavity 32.

Another embodiment, illustrated in FIGS. 7 through 11, provides an alternative fixation technique for the modular prosthesis system 100 of the invention. In this embodiment, the collet is not integral with the fixation peg, but the same modular fixation options exist. That is, fixation pegs can be mounted directly upon the superior surface of a joint prothesis, without an augmentation block, or an augmentation block can be disposed between the fixation peg and the prosthesis.

Figure 7:
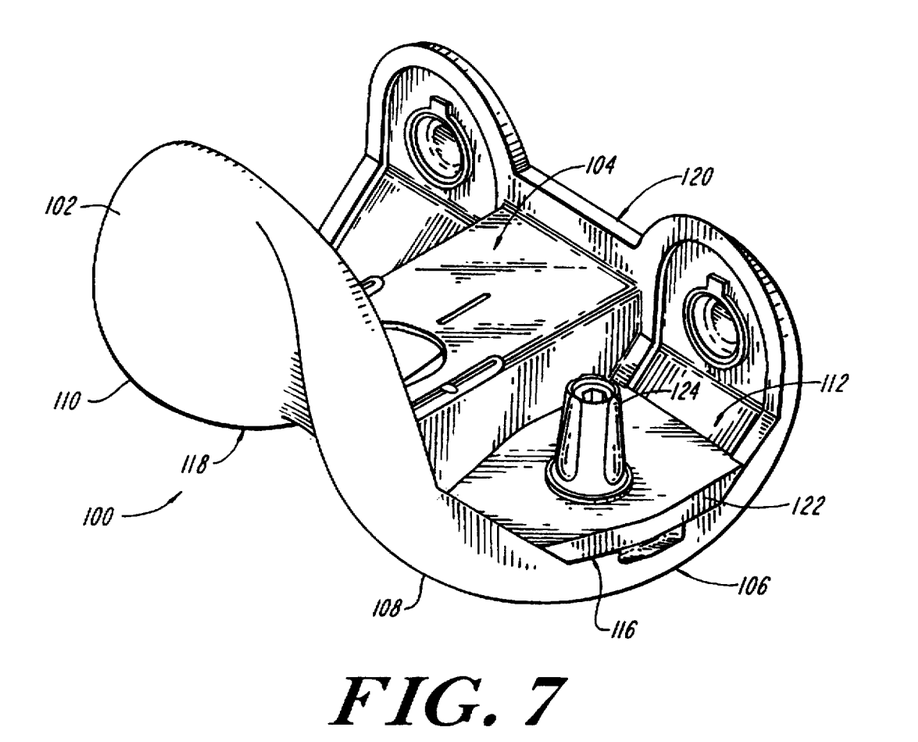
FIG. 7 is an isometric view of an alternative modular augmentation and stabilizing prosthesis system according to the present invention.

FIG. 7 illustrates a cruciate substituting femoral component 102 that includes an intercondylar notch 104, an inferior surface 106 having condyles 108, 110 and a superior bone engaging surface 112 having lateral and medial distal flats. For purposes of illustration, the prosthesis depicted in FIG. 7 is assumed to be a left knee femoral component having anterior 118 and posterior 120 surfaces. Further, FIG. 7 illustrates an augmentation block 122 and fixation peg 124 mounted on lateral distal flat 116. It is understood that the fixation peg 124 can be mounted directly upon the medial or lateral distal flats without an augmentation block.

FIGS. 8A through 11 illustrate the various components of system 100. These components include fixation pegs 124, one or more optional augmentation blocks 122, one or more collets 126 and one or more expansion pins 128. Further, as noted above with respect to FIGS. 1 through 6, the femoral component 102 includes at least one securement cavity 130. Preferably, one securement cavity is mounted on each of the medial and lateral distal flats of the femoral component.

Figure 8A:
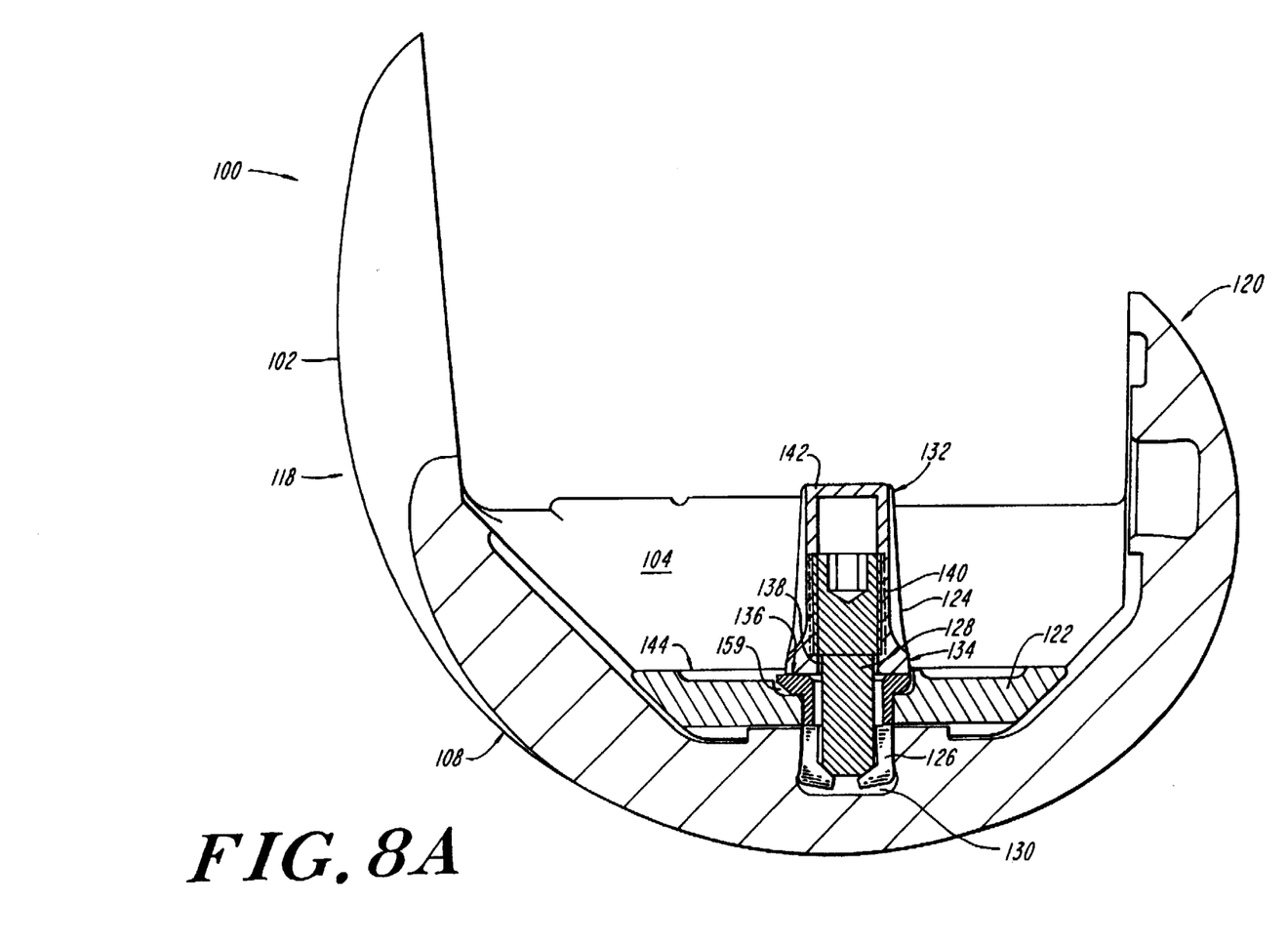
FIG. 8A is a sectional view of the prosthesis system of FIG. 7.
Figure 8B:
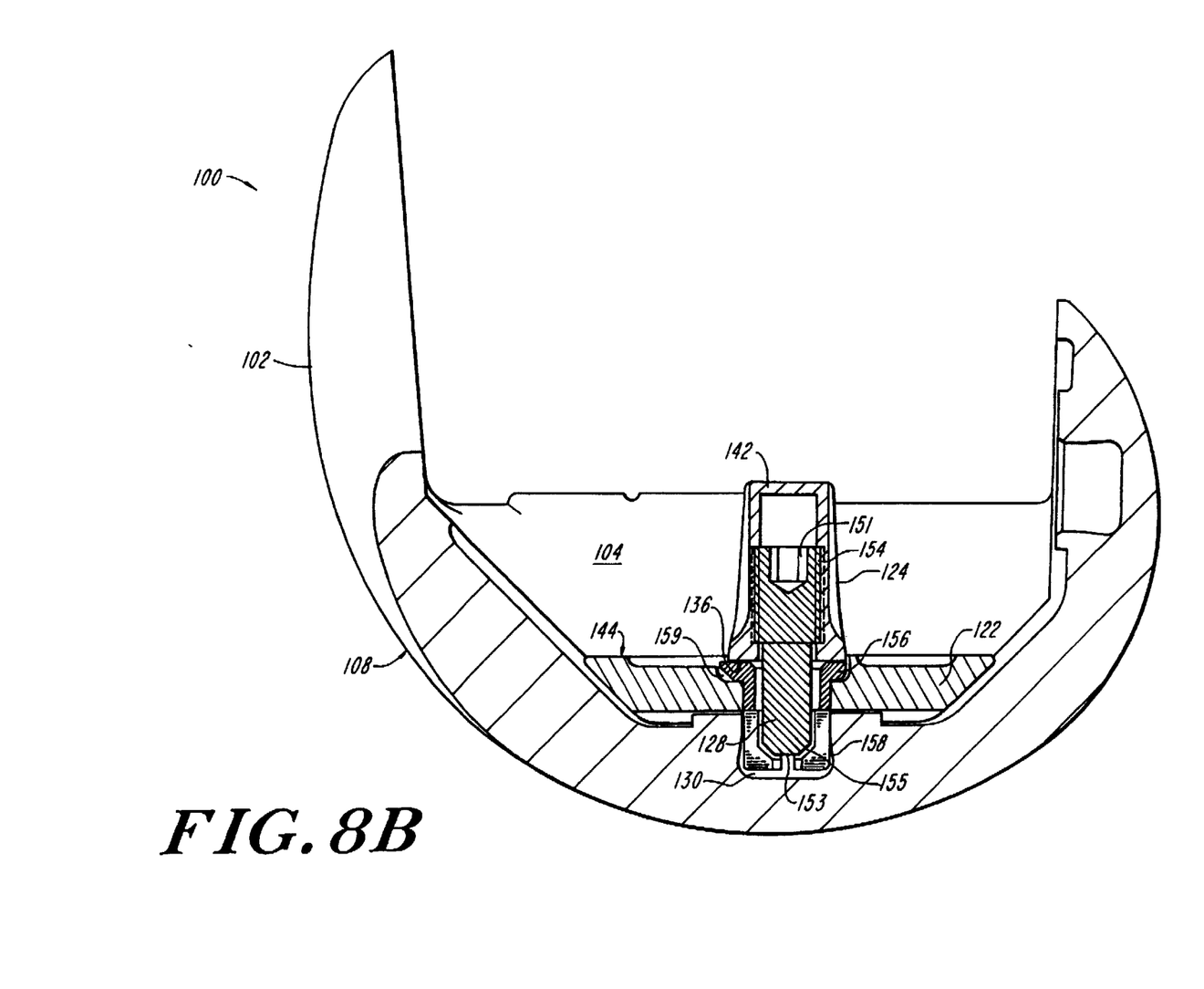
FIG. 8B is a sectional view of the prosthesis system of FIG. 7, illustrating the collet in a non-expanded condition.
Figures 9, 10A, 10B, 10C, 11:
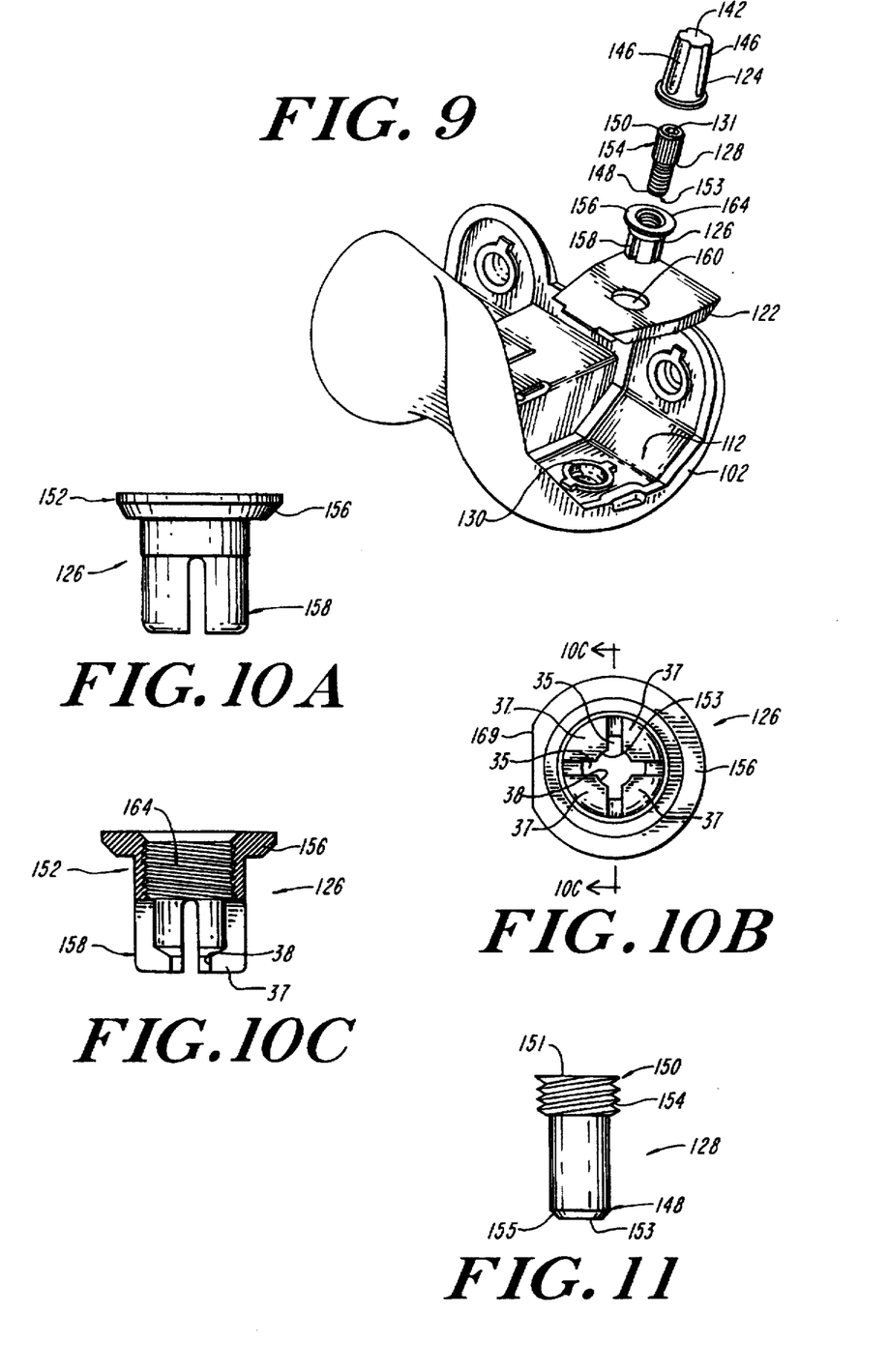
FIG. 9 is an exploded view of the prosthesis system of FIG. 8B.
FIG. 10A is a side view of the collet useful with the invention shown in FIG. 7.
FIG. 10B is a bottom view of the collet shown in FIG. 10A.
FIG. 10C is a sectional view of the collet shown in FIG. 10A.
FIG. 11 is a side view of an expansion pin useful with the invention shown in FIG. 7.

Fixation peg 124 is an elongate member having proximal and distal ends 132, 134. The distal end 134 of the peg includes a base 136 which surrounds an opening 138 of an internal bore 140 which extends within the peg. Internal threads 141 or other internal fixation structures (not shown) preferably are present within the bore and may extend the entire length of the bore or, alternatively, threads be present only in selected regions of the bore. Although the proximal end 132 of peg 126 is shown to include a closed top 142, the top may alternatively be open. The base 136 abuts the proximal surface 144 of augmentation block 122. Alternatively, if no augmentation block is used, base 136 will abut the superior surface 112 of femoral component 102.

Fixation peg 124 is of a construction similar to that described above with respect to FIGS. 1 through 6, except that it does not include an integral distal collet. Fixation peg 124 thus may include external surface features 146 and may have a larger diameter at distal end 134 than at proximal end 132.

As shown in FIGS. 9 and 11, expansion pin 128 is an elongate member that has distal 148 and proximal 150 ends. The expansion pin is intended to expand collet 128, by action of its distal end 148, while its proximal end 150 engages both a proximal end 152 of the collet and the fixation peg. Although various structures can enable the expansion pin to expand the collet and to engage the collet and the fixation peg, a preferred embodiment is described below.

The proximal end 150 of the expansion pin 128 preferably includes external threads 154. Preferably, the threads 154 extend over a distance of about 2 to 20 mm. The distal end 148 of the collet is non-threaded and preferably has a diameter that is slightly less than the diameter of proximal end 150. The distal tip 153 of expansion pin 128 has a geometry that will cause expansion of the collet, such as a radius tip point 155, a dogged end (not shown), or similar geometries. Preferably, the head 151 of the expansion pin 128 is a hex head.

Collet 126 has a proximal end of 152, including collar 156 and a distal, collet expanding end 158. The collar 156 can mount within a recessed area surrounding cavity 130. Alternatively, if an augmentation block 122 is used, the collar 156 will be seated in a recessed area 159 surrounding aperture 160 on a proximal surface 144 of block 122. The collar 156 and the recessed area can be of virtually any corresponding shapes including, for example, circular and D-shaped. A D-shaped collar, which includes a flat end 169, or another irregularly shaped collar, can be useful to prevent any unwanted rotation of the collet within the securement cavity 130 or aperture 160.

As illustrated in FIG. 10C, collet 126 preferably includes internal threads 164 within proximal region 152. These threads are complementary to threads 154 of expansion pin 128 such that a lower (distal) portion of threads 154 mate with threads 164 to maintain the expansion pin in a desired position with the collet. The distal end of the collet is preferably slotted and is of a structure as described above for collet 38 illustrated in FIGS. 1 through 6.

As noted above, FIGS. 7 through 9 illustrate an augmentation block 122 used with system 100. It is understood that the use of augmentation block 122 is optional. If the augmentation block 122 is not to be used, the fixation peg 124 is mounted directly to the superior surface 112 of femoral component 102.

The dimensions of the various components described above can vary depending upon the size and type of prostheses which they are used. One of ordinary skill in the art can readily determine the appropriate dimensions.

System 100 can be utilized as follows. If a surgeon determines that it is desirable to mount fixation pegs 124 upon prosthesis 102, set screw 128 is advanced within collet, without expanding the collet, until threads 154 and 164 mate. The collet is then positioned within securement cavity 130 and the set screw is tightened until the collet expands to the extent that it maintains good purchase upon the inner walls of the securement cavity 130. The torque needed to effect such expansion generally is about 20 to 40 inch-pounds, and more preferably about 30 inch-pounds. Thereafter, the fixation peg is threaded upon expansion pin 128 such that threads 154 mate with internal threads 141 of fixation peg 124. Preferably the length of the external threads 154 that remain exposed once the expansion pin is deployed to expand the collet is about 6 to 12 mm. A similar procedure is utilized for an embodiment in which an augmentation block 122 is to be used. In such embodiment collet 126 may be predisposed within aperture 160 of augmentation block 122. Once the augmentation block is properly positioned on femoral component 102, expansion pin 128 is advanced within the collet causing the collet to expand and to secure the augmentation block to the femoral component. Next, the fixation peg can be threaded upon the proximal end of the expansion pin.

The illustrated embodiments of system 100 include internal threads within the collet 126 and fixation peg 124, and external threads on expansion pin 128. It is understood that other structures can be used, instead of threads, to facilitate joinder of the set screw to both the collet and the fixation peg.

The prostheses components of the invention can be made from a variety of biocompatible materials having high strength, durability and resistance to wear debris. Examples of such materials include metal alloys such as a cobalt chromium alloys, titanium alloys, stainless steel, ceramics and other materials, including polymers, that are well known for use in the manufacture of implantable bone prostheses. A preferred material for the prostheses components is a cobalt chromium alloy such as ASTM F-75.

The collet components preferably are made from a malleable metal or metal alloy to reduce the risk of tensile failure as a result of collet expansion. Where such materials are used to form a threaded component, the materials should be able to deform (but not fail) when subjected to a torque of about 20 to 65 in-lbs, and more preferably about 25-35 in-lbs. A preferred material is a wrought cobalt chromium alloy such as ASTM F-90.

The set screw preferably is made from a metal or metal alloy that has a higher modulus and a greater hardness than does the collet. Such properties ensure that the collet (and not the expansion pin) will deform when subjected to torque and/or axial load. A preferred material from which the expansion pin can be manufactured is wrought cobalt chromium alloy such as ASTM F-1537 (formerly known as ASTM F-799).

The tensile securement values of the fixation pegs and/or augmentation blocks to the femoral components preferably are in the range of about 50 to 500 kg. This secure fit ensures that the performance of the prosthesis component is not compromised. Moreover, the modular fixation peg and augmentation system of the invention can be easily attached within a femoral component of a knee joint prosthesis.

The foregoing description of the illustrative embodiment of the invention is presented to indicate the range of constructions to which the invention applies. Variations in the physical architecture and dimensions of the invention will be apparent to those having ordinary skill in the art based upon the disclosure herein, and such variations are considered to be within the scope of the invention in which patient rights are asserted, as set forth in the claims appended hereto. All publications and references cited herein are expressly incorporated herein by reference in their entirety.

What is claimed is:

1. A modular knee joint prosthesis system, comprising
a femoral component having a superior bone engaging surface and an inferior articulation surface, the superior surface including at least one securement cavity, wherein the at least one securement cavity is defined by a sidewall and a bottom wall;
at least one fixation peg member, wherein the at least one fixation peg member is selectively matable with the at least one securement cavity of the superior surface of the femoral component, the at least one fixation peg member having a distal end, a proximal bone engaging end and an internal bore;
at least one collet member matable with a distal end of the at least one fixation peg member to selectively mate the at least one fixation peg member to the at least one securement cavity, wherein the at least one collet member has an expandable distal end adapted to fit within and selectively engage the sidewall of the at least one securement cavity and a proximal end including an internal bore, and
at least one expansion pin element having a proximal end including an external structure matable with the internal bore of the at least one fixation peg member and the internal bore of the at least one collet member, and a distal end capable of selectively expanding the at least one collet member such that the at least one collet member engages to the at least one securement cavity.

2. The system of claim 1, wherein the internal bore of the at least one fixation peg member includes an internally threaded portion.

3. The system of claim 2, wherein the internal bore of the at least one collet member includes an internally threaded portion.

4. The system of claim 3, wherein the external structure of the at least one expansion pin element comprises an external threaded region.

5. The system of claim 1, wherein the at least one collet member is integral with the at least one fixation peg and forms a distal end thereof.

6. The system of claim 4, wherein the at least one collet member is separate from the at least one fixation peg member, and wherein the at least one collet member includes
an expandable distal end formed by two or more expandable wedge-like members each separated by a slot; and
a collar at a proximal end thereof.

7. The system of claim 6, wherein the collar of the at least one collet member seats upon the at least one securement cavity with the distal end of the at least one collet member extending therein such that the at least one expansion pin element is threadingly engaged within the internally threaded region of an axial bore of the at least one collet member and the internally threaded region of the at least one fixation peg member.

8. The system of claim 7 further comprising at least one augmentation block having first and second opposed surfaces and an aperture extending therebetween, the first surface of the at least one augmentation block being mountable upon a portion of the superior surface of the femoral component and the aperture being dimensioned to receive the distal end of the at least one collet member such that the at least one augmentation block and the at least one fixation peg member are together selectively matable with an articulation component.

9. The system of claim 8 wherein the articulation component is a femoral component of a knee joint prosthesis.

10. The system of claim 8 wherein in the femoral component is a cruciate substituting femoral component including an intercondylar notch formed on the superior surface thereof.

11. The system of claim 10, wherein the at least one securement cavity is formed on each of a medial distal flat and a lateral distal flat of the femoral component.

12. The system of claim 4, wherein the at least one fixation peg member has a length in the range of 2 to 60 mm.

13. The system of claim 8, wherein the at least one fixation peg member decreases in diameter from an end adjacent one of the superior surface of the at least one augmentation block and the superior surface of the articulation component to the proximal end thereof.

14. The system of claim 13, wherein the at least one fixation peg member includes external surface features.

15. The system of claim 14 wherein the external surface features are selected from the group consisting of axial ribs, axial grooves, annular ribs and annular grooves.

16. The system of claim 4, wherein the at least one collet member has two or more wedge-shaped structures at a distal end thereof.

17. The system of claim 13, wherein the bore formed in the at least one fixation peg member extends from an opening in the distal end to a closed proximal end.

18. A modular joint prosthesis system, comprising:

an articulation component having a first, bone engaging surface and a second, articulation surface, the first surface including at least one securement cavity, wherein the at least one securement cavity is defined by a sidewall and a bottom wall;

at least one fixation peg member, wherein the at least one fixation peg member is selectively matable within the at least one securement cavity on the first surface of the articulation component and the at least one fixation peg member has a distal end including at least one collet member that is engageable with the at least one securement cavity, a proximal bone engaging end and an axial bore extending between the distal and proximal ends of the at least one fixation peg member; and at least one expansion pin element having a proximal end including at least one external structure matable within the axial bore of the at least one fixation peg member, the at least one expansion pin element further including a distal end capable of selectively expanding the at least one collet member such that the at least one collet member engages with the at least one securement cavity.

19. The system of claim 18, wherein an axial bore of the at least one fixation peg member includes an internally threaded region.

20. The system of claim 19, wherein the at least one external structure of the at least one expansion pin element comprises a threaded region.

21. The system of claim 20 further comprising at least one augmentation block having first and second opposed surfaces and an aperture extending therebetween, the first surface of the at least one augmentation block being mountable upon the first surface of the articulation component, and the aperture being dimensioned to receive the at least one fixation peg member such that the at least one augmentation block and the at least one fixation peg are together selectively matable with the articulation component.

22. The system of claim 21 wherein the articulation component is a femoral component of a knee joint prosthesis.

23. The system of claim 21 wherein the femoral component is a cruciate substituting femoral component including an intercondylar notch formed on the first surface thereof.

24. The system of claim 22, wherein the at least one securement cavity is formed on each of the medial distal flat and the lateral distal flat of the femoral component.

25. The system of claim 20, wherein the at least one fixation peg member has a length in the range of 2 to 60 mm.

26. The system of claim 25, wherein the at least one fixation peg member decreases in diameter from the distal to the proximal end thereof.

27. The system of claim 25, wherein the at least one fixation peg member includes external surface features.

28. The system of claim 27, wherein the external surface features are selected from the group consisting of axial ribs, axial grooves, annular ribs and annular grooves.

29. The system of claim 20, wherein the at least one collet member has two or more wedge-shaped structures at a distal end thereof.

30. A modular joint prosthesis system, comprising:

an articulation component having a first, bone engaging surface and a second, articulation surface and at least one securement cavity formed in the first surface, wherein the at least one securement is defined by a sidewall and a bottom wall;

at least one fixation peg member, wherein the at least one fixation peg member is selectively matable with the at least one securement cavity on the first surface of the articulation component, the at least one fixation peg member having a distal end, a proximal bone engaging end and an axial bore formed therein, the axial bore including internal threads;

at least one collet member having a distal end including two or more expandable wedge elements that are able to selectively engage the with the at least one securement cavity and a bore extending therethrough, at least a proximal portion of the bore including an internally threaded portion; and at least one expansion pin element having a distal end able to expand the distal end of the at least one collet member and a proximal end including external threads, the at least one expansion pin element being insertable within the axial bore of the at least one fixation peg and the at least one collet member such that the external threads of the at least one expansion pin element mate with the internal threads of the at least one fixation peg and the internally threaded portion of the at least one collet member.

31. The system of claim 30, wherein the at least one collet member is integral with the distal end of the at least one fixation peg member.

32. The system of claim 30 further comprising an augmentation block having a first surface mountable upon a portion of the first surface of the articulation component, a second opposed surface and an aperture extending between the first and second surfaces.

* * * * *

UNITED STATES PATENT AND TRADEMARK OFFICE
CERTIFICATE OF CORRECTION

PATENT NO. : 5,766,255
DATED : June 16, 1998
INVENTOR(S) : John E. Slamin; Michael J. O'Neil; Jason T. Gulbinas It is certified that error appears in the above-indentified patent and that said Letters Patent is hereby corrected as shown below:

In the Claims:

Claim 30, column 12, line 23 after "securement" please insert -- cavity --.

Signed and Sealed this

Third Day of November, 1998

*Attest:*

BRUCE LEHMAN

*Attesting Officer*     *Commissioner of Patents and Trademarks*